United States Patent [19]

Butterworth et al.

[11] 4,077,410

[45] Mar. 7, 1978

[54] DISPOSABLE ABSORBENT PAD WITH NON-WOVEN FACING

[75] Inventors: George A. M. Butterworth, Western Springs; Robert T. Elias, Downers Grove, both of Ill.

[73] Assignee: Johnson & Johnson, New Brunswick, N.J.

[21] Appl. No.: 702,397

[22] Filed: Jul. 6, 1976

[51] Int. Cl.² .................... A41B 13/02; A61F 13/16
[52] U.S. Cl. .................................. 128/287; 128/156; 128/284
[58] Field of Search .................. 128/284, 287, 156

[56] References Cited

U.S. PATENT DOCUMENTS 3,804,092  4/1974  Tunc .................................. 128/284
3,987,792  10/1976  Hernandez et al. ................. 128/287
3,994,299  11/1976  Karami ............................... 128/284

*Primary Examiner*—Leland A. Sebastian

[57] ABSTRACT

A disposable absorbent pad such as a diaper, sanitary napkin, underpad, surgical dressing or wipe, and the like, is made from a flexible, body fluid-impermeable backing sheet, a layer of absorbent material on the backing sheet, and a soft, body fluid-permeable facing sheet which overlies the absorbent material. The facing sheet is a non-woven, open but interconnected network of oriented thermoplastic polymer fiber elements having a mean denier of not more than 3. In addition to being useful as a separate entity, the absorbent pad of this invention can also be incorporated into a disposable or limited use garment as an integral part thereof.

18 Claims, 4 Drawing Figures

DISPOSABLE ABSORBENT PAD WITH NON-WOVEN FACING

BACKGROUND OF THE INVENTION

This invention relates to disposable absorbent pads such as diapers, sanitary napkins, underpads, surgical dressings and wipes, and the like.

Non-woven, bonded, textile/pulp fabrics, hydraulically-entangled and mechanically-bonded textile fiber fabrics, and relatively thin, spun-bonded fabrics are the usual facing fabrics for disposable sanitary and convenience products. Such fabrics should be relatively soft and conformable, capable of extended contact with external and internal body surfaces without causing chafing or allergenic reactions, and also capable of transmitting body fluids to a central absorbent core or layer while maintaining skin dryness. However, such facing fabrics are relatively expensive inasmuch as synthetic polymeric materials must be first converted to textile filaments or fibers, and the synthetic or natural textile length fibers must be further converted into a web structure and mechanically, hydraulically, or adhesively bonded to produce a facing fabric which meets the aforementioned requirements.

In order to minimize the cost of disposable sanitary and convenience products it is desirable to develop disposable absorbent pads which do not utilize a fabric-type facing sheet yet which retain the above comfort and conformability characteristics.

U.S. Pat. No. 3,431,911 to Meisel discloses an absorbent pad having a facing layer made of reticulated polymeric foam, such as polyurethane foam, which is disposed over an underlying layer of fluid absorbent material. However, foamed facing layers have a coarse structure, are relatively bulky, and tend to increase the overall dimensions of the absorbent pad. Moreover, the open-cell structure of the foam layer may cause undesirable reverse pumping action when an absorbent pad of such type is compressed while being used. In addition, foam surfaces do not have the desired surface aesthetics.

U.S. Pat. No. 3,901,240 to Hoey discloses a liner of crushed, thermosettable polymeric latex foam for an absorbent pad, which liner disintegrates when the absorbent pad is flushed away. However, the liner has relatively low cohesive strength and is relatively dense and bulky.

In our copending application, U.S. Ser. No. 591,747, filed on June 30, 1975, now U.S. Pat. No. 3,967,623, are disclosed absorbent pads having a facing which is a perforate, substantially hydrophobic web of a thermoplastic polymeric material provided with an integral fibrous outer surface. We have now found that the bulkiness of an absorbent pad can be reduced and conformability of the pad to the user enhanced by providing a body fluid-permeable facing which is a relatively thin non-woven fibrous web made up of interconnected, molecularly oriented fiber elements having a fine denier.

SUMMARY OF THE INVENTION

The present invention contemplates an absorbent pad which provides the desirable characteristics of a woven fabric facing material but at a reduced cost. The absorbent pad comprises a flexible backing sheet impermeable to body fluids, a layer of absorbent material on the backing sheet, and a soft, body fluid-permeable, non-woven facing fabric or sheet which overlies the absorbent material. The facing sheet is a non-woven, open but interconnected network of molecularly oriented, thermoplastic polymer fiber elements having a mean denier of not greater than 3. The fiber elements are molecularly oriented substantially in the plane of the facing sheet. The facing sheet can comprise a plurality of plies having different wettability characteristics with respect to body fluids. Alternatively, a surface active agent, e.g., the sodium salt of dioctyl sulfosuccinate, or the like, can be deposited on the facing sheet or incorporated into the thermoplastic fiber elements thereof to control surface wettability and to promote body fluid transmission or transport through the facing sheet.

The absorbent pads of this invention absorb body fluids and are useful as disposable diapers, sanitary napkins, underpads, surgical dressings and wipes. The absorbent pads can be used as separate entities, or can be integral parts of a disposable or a limited use garment.

DESCRIPTION OF PREFERRED EMBODIMENTS

Figure 1:
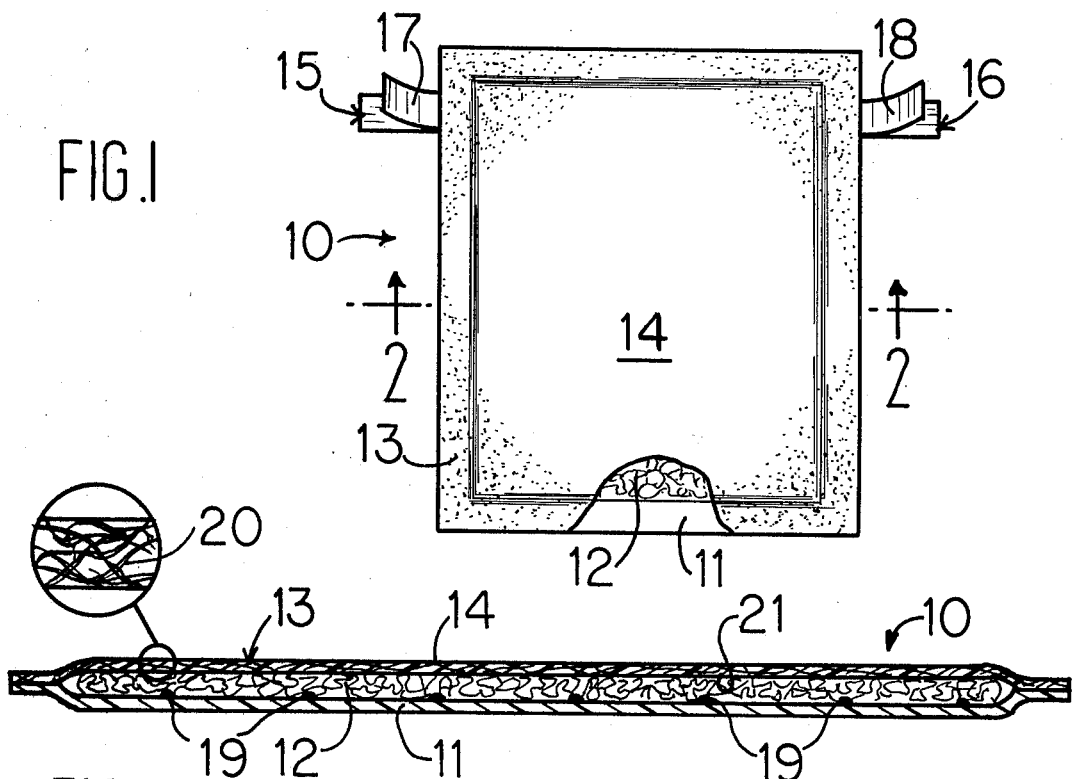
FIG. 1 is a plan view showing a disposable diaper embodying the present invention.
Figure 2:
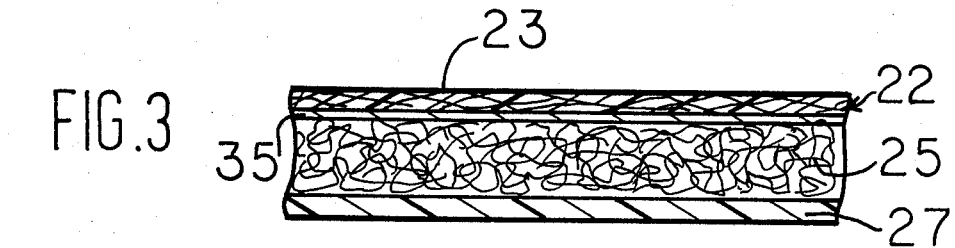
FIG. 2 is a sectional elevation on an enlarged scale taken along plane 2—2 in FIG. 1 and further showing a substantially enlarged section of the contemplated facing sheet for the diaper.

As illustrated in FIGS. 1 and 2, an absorbent pad of this invention, such as disposable diaper 10, comprises flexible backing sheet 11, absorbent panel 12 which is a layer of fluffy absorbent material positioned on backing sheet 11, and facing sheet 13 which is a non-woven, open but interconnected network of oriented, thermoplastic fiber elements 20. During use, outer surface 14 of facing sheet 13 is in contact with or faces the user of the absorbent pad. Diaper 10 is also equipped with fastening tabs 15 and 16 which comprise a pressure-sensitive adhesive layer on a flexible backing or substrate. The adhesive layer on each tab is protected prior to use by removable cover strips 17 and 18 which are segments of paper or similar web-like material bearing a suitable release compound on the side thereof in contact with the adhesive layer. Alternatively, cover strips 17 can be permanently anchored to facing sheet 13, thereby eliminating the need for the separate disposal thereof.

Facing sheet 13 and backing sheet 11 usually are substantially coextensive and are joined together about the periphery of diaper 10 by thermal fusion, adhesive, or in any other convenient manner. If desired, absorbent layer or panel 12 can be anchored to backing sheet 11 by one or more glue lines 19. A suitable backing sheet material can be an opaque polyolefin, e.g., polyethylene, web impermeable to body fluids and about 0.001 inch thick. Another suitable sheet material for this purpose is a polyester, e.g., polyethylene terephthalate, web having a thickness of about 0.0005 inch.

Absorbent panel 12 can be a fluffy batt cut from a relatively loose web of non-woven fibers having a relatively high absorptive capacity. Panel 12 usually is of a rectangular configuration and somewhat smaller than backing sheet 11. Particularly suitable absorbent layers or panels can be made in accordance with the teachings of U.S. Pat. No. 3,612,055 to Mesek et al.

Absorbent panel 12 can also be a fibrous batt having an integral densified layer. In such a case panel 12 is positioned on the backing sheet of the absorbent pad so that the densified layer adjoins the backing sheet. The densified layer has relatively higher wettability and liquid retentivity than the rest of the aforesaid batt and usually is formed by slightly moistening one surface of the batt and thereafter compressing the moistened surface. The nature of the batt having an integral densified layer as well as the method of producing same are described in detail in U.S. Pat. No. 3,017,304 to Burgeni.

Facing sheet 13 is readily permeable to body fluids and is made up of an open network of interconnected fiber elements 20 which are of a very fine denier, i.e., a mean denier not greater than about 3 and usually about 0.1 to about 3. A mean denier of about 0.25 to about 1.5 is preferred. Additionally, the soft, fibrous outer surface 14 can be provided with fine fibrils extending away from surface 14. These fine fibrils are integral with facing sheet 13 and further enhance the feel of facing sheet 13 as will be discussed in greater detail hereinbelow. Fiber elements 20 are composed of a molecularly oriented thermoplastic polymer the degree of crystallinity and orientation of which can be ascertained by known X-ray diffraction techniques. Preferably the oriented polymers exhibit a birefringence greater than about 0.005, and more preferably a birefringence greater than about 0.01. The bulk density of facing sheet 13 is generally about 0.05 to about 0.15 g./cc., and preferably about 0.075 to about 0.1 g./cc. Thus the absorbent pads of the present invention provide a facing which is relatively light in weight and thin (i.e., not bulky), yet which exhibits considerable strength because of the presence of fiber elements which are molecularly oriented.

Facing sheets comprising the desired open but interconnected network of oriented thermoplastic polymer fibers having fine denier can be conveniently made by forming a foamed melt of the thermoplastic polymer, extruding the melt through a suitable die, cooling the extruded mass to orientation temperature (i.e., a temperature slightly above the softening temperature for the polymer), and thereafter hot drawing the extruded mass into a coherent sheet of interconnected, oriented fibers having the desired denier, followed by cooling to ambient temperature. The hot drawing can be unidirectional or bidirectional depending on whether unidirectional or bidirectional orientation of produced fiber elements is desired. In either event, however, the molecular orientation of the fiber elements forming the interconnected network is substantially in the plane of the produced facing sheet. In some cases, the attained orientation can be set and the sheet stabilized by annealing the produced facing sheet.

Facing sheets having varying wettability and other characteristics can be produced by coextruding foamed melts of different polymer composition so as to produce an interconnected network of oriented fiber elements having one composition on one side of the facing sheet and an integral interconnected network of oriented fiber elements having another composition on the other side of the facing sheet. Methods of producing a facing sheet for the absorbent pads of the present invention are known in the art. One such method is disclosed in U.S. Pat. No. 3,403,203 to Schirmer whereby non-woven fabrics are produced by extruding a foamable thermoplastic composition so as to form an elongated cellular member, elongating the cells in the extruded member sufficiently to rupture at least the majority of the individual cells, and cooling the resultant member. The foamable thermoplastic composition is extruded through an annular die into an area of reduced pressure so as to form a seamless cellular tube which is then inflated and thus biaxially stretched. Thereafter the inflated structure is cooled, deflated and slit to form a sheet. A similar method and the non-woven fabric produced thereby is disclosed in U.S. Pat. No. 3,717,541 to Schirmer.

Another suitable non-woven fabric comprising an open structure made up of interconnecting thermoplastic polymer fiber elements and the method of manufacture therefor are shown in Canadian Pat. No. 933,718 to Baxter. The desired denier of the interconnected fiber elements is obtained by selecting the appropriate draw ratio for the particular extruded, foamed thermoplastic polymer that is utilized.

The thickness of the facing sheet that is provided for the absorbent pads of the present invention can vary, depending on the intended end use of the pads. Usually the facing sheet is about 1 mil to about 10 mils thick.

Facing sheets produced in the foregoing manner usually have a good drape and hand, and a relatively smooth surface. For certain absorbent pads, such as diapers or for pads which are provided as an integral part of a disposable garment, it may be desirable to provide a napped surface on the facing sheet. To this end, the draw ratio of the extruded mass can be increased to the point where the produced finer denier fiber elements begin to break and provide fiber ends which project away from the outer surface of the facing sheet for a small distance so as to give a fuzzy or velvet-like appearance and feel to the facing sheet.

A similar appearance can be provided for the facing sheet by a mechanical after-treatment of the facing sheet outer surface, for example, by brushing, abrading, or similar treatments which break a portion of the interconnected fiber elements at the surface.

If desired, the produced facing sheet can be stabilized or consolidated by point-embossing the entire sheet or selected regions thereof where additional strength is deemed necessary. Point-embossing can be performed utilizing heat-bonding or ultrasonic sealing techniques known in the art. To produce a tufted absorbent pad and stabilize the absorbent layer of the pad, the facing sheet can be point-embossed at spaced locations after the absorbent pad has been assembled so as to join the facing sheet to the backing sheet through the absorbent layer.

Moreover, the facing sheet can be sprayed or selectively printed with a curable liquid binder (e.g., cross-linkable acrylic monomer latex) so as to form binder nodules within the interconnected fiber element network which nodules are subsequently solidified, for example, by curing.

Facing sheets suitable for the present absorbent pads are made from foamed melts of orientable thermoplastic polymers such as polyolefins (e.g., polyethylene, polypropylene), polyesters (e.g., polyethylene terephthalate), polyacrylonitrile polyvinyl chloride, polyvinylidene chloride, polycaprolactams, polyamides, polystyrene, and the like. Also suitable are blends of the foregoing polymeric materials which can be extruded as a foamed mass and then hot drawn approximately to a three- to 15-fold elongation. Particularly preferred for the present purposes are the polyolefins and blends of a polyolefin with a textile fiber-making polymer such as a polycaprolactam. In such blends the amount of each ingredient present can vary from about 10 weight percent to about 80 weight percent, depending on the properties desired in the ultimate end product.

Inasmuch as the wettability of the non-woven, open network structures by body fluids is dependent to a considerable extent on the nature of the polymeric material that is used to make up the structure, the wettability of the facing sheet can be tailored by an appropriate selection of the polymer blend that is used for fabrication of the facing sheet. For example, a polyolefin is a hydrophobic, i.e., non-wetting, material whereas a polycaprolactam (e.g., nylon 6) or a polyamide is a relatively hydrophilic, i.e., wetting, material. Thus, a blend having a relatively high polycaprolactam or polyamide content can be selected if it is desired to produce a wettable facing sheet, and a blend having a relatively high polyolefin content can be selected for producing a relatively non-wettable facing sheet.

For disposable diapers it is generally desirable to have a facing sheet with a non-wetting outer surface so that the portion of the diaper in contact with an infant's skin remains relatively dry even after the infant has voided. However, for enhanced body fluid transport away from the infant it is desirable to have a readily wettable structure which aids in transporting the body fluids to the absorbent panel. In the disposable diapers constructed according to the present invention both conditions can be readily achieved in the same facing sheet by providing a plurality of superposed plies having progressively increasing wettability in the direction of desired liquid, i.e., body fluid, transport. That is, facing sheet 13 can be made up, for example, having an outer ply of interconnected polyethylene fiber elements, an intermediate ply of interconnected fiber elements derived from a polyethylene-polycaprolactam blend, and an inner ply of interconnected polycaprolactam fiber elements.

In lieu of or in addition to the foregoing built-in wettability control, a relatively wettable facing sheet can be made less wettable, either in selected regions thereof or throughout, by treatment with a thermosetting binder (e.g., a curable acrylic latex composition) which at the same time can impart additional strength to the facing sheet, if desired.

Facing sheet 13 can also be treated with a surface active agent or mixtures thereof, for example, with the sodium salt of dioctyl sulfosuccinate (commercially available under the designation Aerosol OT), non-ionic polyoxyethylene sorbitan monolaurate (commercially available under the designation Tween 20), or the like, by spraying an aqueous solution of the desired surface active agent onto outer surface 14 and subsequent drying. The surface active agent can also be deposited on facing sheet 13 by means of a roller wet with an aqueous solution of the surface active agent which is passed over inner surface 21 of facing sheet 13 so as to deposit the surface active agent near and on inner surface 21 while fibrous outer surface 14 retains a substantially hydrophobic character. In the alternative, internal surfactants or wetting agents can be incorporated directly into the thermoplastic polymer during manufacture of the facing sheet. Suitable wetting agents for the latter purpose can be non-ionic surfactants based on ethylene oxide-fatty alcohol ethers, ethoxylated adducts of propylene oxide with propylene glycol, fatty esters or sorbitol and glycerol, and the like.

Figure 3:
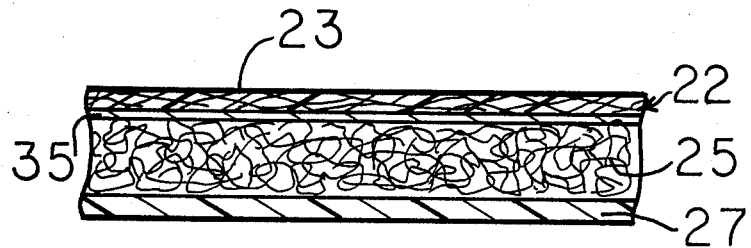
FIG. 3 is a fragmentary sectional elevation on an enlarged scale illustrating a further embodiment of this invention.

Another embodiment of this invention is illustrated in FIG. 3. Facing sheet 22 made of oriented polyethylene fiber elements interconnected to form an open network of about 1 denier overlies absorbent layer 25. A thin web of absorbent tissue such as web 35 is positioned between facing sheet 22 and absorbent layer 25 and functions as a wicking sheet for the excreted body fluids. Absorbent web 35 also assists in the distribution of body fluids over the lateral surface of absorbent layer 25. If desired, absorbent web 35 can be impregnated with a surface active agent; however, in many instances it is not necessary to do so, especially if web 35 is made from a cellulosic material. Polyethylene backing sheet 27 provides a liquid barrier which retains absorbed liquids within the pad and is fused to facing sheet 22 about the periphery of the pad by heat sealing techniques, ultrasonic sealing techniques, or the like.

Figure 4:
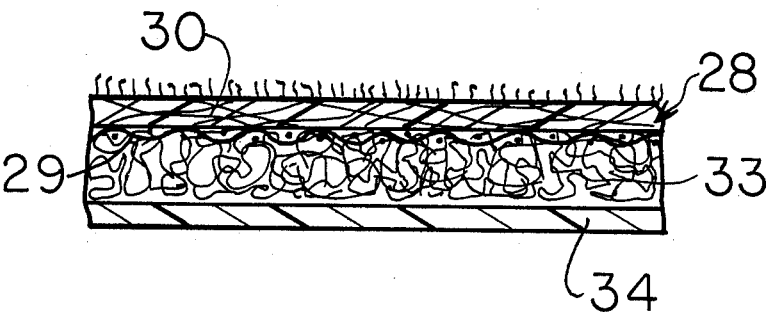
FIG. 4 is a fragmentary sectional elevation on an enlarged scale illustrating yet another embodiment of the present invention.

A still further embodiment of this invention is shown in FIG. 4. Facing sheet 28 covers fibrous absorbent batt 33 which rests on backing sheet 34, reinforced by underlying scrim 29, and is provided with napped, i.e., fibrous, outer surface 30 produced by mechanical aftertreatment such as brushing, abrading, sueding, or the like. A surface active agent, e.g., the sodium salt dioctyl sulfosuccinate, is deposited as a srpay on the fiber elements of facing sheet 28 and promotes liquid transport from outer surface 30 to absorbent batt 33.

Scrim 29 provides further support or reinforcement for facing sheet 28 and preferably is made of a thermoplastic material which can be readily bonded to facing sheet 28. One such scrim material is disclosed in U.S. Pat. No. 3,666,609 to Kalwaites et al. Other suitable scrim materials are described in U.S. Pat. No. 3,914,365 to Kim et al. and in U.S. Pat. No. 3,441,638 to Patchell et al. If the scrim material is thermoplastic and extendable as taught in the latter two patents, the scrim material can serve as support for the extruded foamed polymeric mass which is the precursor of the facing sheet, and can be extended as the extruded mass is hot drawn to produce the interconnected fiber elements of desired denier. At the same time, the hot extruded mass will fuse with the extendable scrim material and form a permanent bond upon cooling without more.

The absorbent pads of the present invention can be of various shapes and configurations depending on the intended end use, e.g., as disposable diapers, sanitary napkins, underpads, surgical dressings or wipes, and the like. Additionally, the present absorbent pads can be incorporated into a disposable or limited use garment as an integral part thereof. For example, an absorbent pad made according to the present invention can be a part of disposable training pants and similar garments.

The foregoing description and the drawing are intended as illustrative and are not to be taken as limiting. Still other variations are possible without departing from the spirit and scope of this invention and will readily present themselves to one skilled in the art.

We claim:

1. An absorbent pad comprising a flexible, body fluid-impermeable backing sheet, a layer of absorbent material on said backing sheet, and a soft, body fluid-permeable facing sheet overlying said absorbent material; said facing sheet being non-woven, open but interconnected network of molecularly oriented, thermoplastic polymer fiber elements having a mean denier of not greater than 3; said facing sheet having a bulk density of about 0.05 grams/cubic centimeter to about 0.15 grams/cubic centimeter, said fiber elements exhibiting a birefringence greater than 0.005 and being molecularly oriented substantially in the plane of the facing sheet.

2. The absorbent pad in accordance with claim 1 wherein the outer surface of said facing sheet is napped.

3. The absorbent pad in accordance with claim 1 wherein said facing sheet comprises a plurality of plies having different wettability with respect to body fluids.

4. The absorbent pad in accordance with claim 3 wherein the outermost ply of said plurality of plies is least wettable with respect to body fluids.

5. The absorbent pad in accordance with claim 1 wherein said molecularly oriented fiber elements exhibit a birefringence greater than about 0.01.

6. The absorbent pad in accordance with claim 1 wherein said network of molecularly oriented fiber elements is point-bonded at spaced intervals.

7. The absorbent pad in accordance with claim 1 wherein said facing sheet has a bulk density of about 0.075 grams/cubic centimeter to about 0.1 grams/cubic centimeter.

8. The absorbent pad in accordance with claim 1 wherein said fiber elements have a mean denier of about 0.25 to about 1.5.

9. The absorbent pad in accordance with claim 1 wherein said thermoplastic fiber elements are made from a polyolefin.

10. The absorbent pad in accordance with claim 1 wherein said thermoplastic fiber elements are made from a blend of a polyolefin and a polycaprolactam.

11. The absorbent pad in accordance with claim 1 wherein said thermoplastic fiber elements are made from polyethylene.

12. The absorbent pad in accordance with claim 1 wherein said thermoplastic fiber elements are made from polypropylene.

13. The absorbent pad in accordance with claim 1 wherein a surface active agent is present on said facing sheet.

14. The absorbent pad in accordance with claim 1 wherein a carrier scrim is associated with said facing sheet.

15. The absorbent pad in accordance with claim 1 wherein a wicking sheet is provided between said facing sheet and said layer of absorbent material.

16. The absorbent pad in accordance with claim 1 wherein a surface active agent is incorporated into said fiber elements.

17. The absorbent pad in accordance with claim 1 wherein a polymeric binder is present in said facing sheet.

18. A disposable garment including, as an integral part thereof, an absorbent pad comprising a flexible, body fluid-impermeable backing sheet, a layer of absorbent material on said backing sheet, and a soft, body fluid-permeable facing sheet overlying said absorbent material; said facing sheet being a non-woven, open but interconnected network of molecularly oriented, thermoplastic fiber elements having a mean denier of not greater than about 3; said fiber elements being molecularly oriented substantially in the plane of the facing sheet.

* * * * *